(12) United States Patent
Cooper et al.

(10) Patent No.: US 6,331,658 B1
(45) Date of Patent: Dec. 18, 2001

(54) GENETICALLY ENGINEERED MAMMALS FOR USE AS ORGAN DONORS

(75) Inventors: David K. C. Cooper; Eugen Koren, both of Oklahoma City, OK (US)

(73) Assignees: Integris Baptist Medical Center, Inc.; Oklahoma Medical Research Foundation, both of Oklahoma City, OK (US)

( * ) Notice: Subject to any disclaimer, the term of this patent is extended or adjusted under 35 U.S.C. 154(b) by 0 days.

(21) Appl. No.: 08/379,040

(22) Filed: Jan. 27, 1995

Related U.S. Application Data

(63) Continuation of application No. 08/049,817, filed on Apr. 20, 1993, now abandoned.

(51) Int. Cl.$^7$ .......................... C12N 15/09; C12N 15/63; C12N 15/00; C12N 5/00
(52) U.S. Cl. ................................ 800/14; 800/17; 800/21; 800/22; 800/25; 800/8; 800/9; 800/3; 435/455; 435/320.1; 435/325; 435/69.1
(58) Field of Search .................................. 800/2, 3, 13, 8, 800/9, 21, 14, 17, 22, 25; 435/172.1, 172.2, 172.3, 1, 97, 193, 320.1, 455, 325, 69.1; 514/44; 424/9.2

(56) References Cited

U.S. PATENT DOCUMENTS 5,849,991 * 12/1998 D'Apice .................................... 800/2
6,166,288 * 12/2000 Diamond et al. ....................... 800/17

OTHER PUBLICATIONS

Mollnes et al., Molecular Immunology, vol. 36, Issue 4–5, pp. 269–276, Mar. 1999.*
Piedrahita, Theriogenology, vol. 53, pp. 105–116, 2000.*
Capecchi, Scientific American, vol. 270, No. 3, pp. 34–41, Mar. 1994.*
Chen et al. Transplantation. 65 (6): 832–837, Mar. 1998.*
Dorling et al. Lancet. 349: 867–871, Mar. 1997.*
Cooper, et al. Lancet. 342: 682–683, Dec. 1993.*
Good et al. Transplantation Proceedings. 24(2):559–562, Apr. 1992.*
Galili et al. Journal of Biological Chemistry. 263(33): 17755–17762, 1988.*
Bradley et al. Biotechnology. 10: 534–539, May 1992.*
Larsen et al. J. of Biological Chemistry. 265(12): 7055–7061, Apr. 1990.*
Gustafsson et al., 1994 Immunological Reviews 141:59–70.*
Sandrin et al. 1994. Xenotransplantation 1:81–88.*
Fodor et al. 1994. Proc. Natl Acad Sci, USA, 91: 11153–11157.*
Dabkowski et al. 1993. Transplanation Proceedings 25(5):2921.*
Sandrin et al. 1993. Proc. Natl Acad Sci, USA 90:11391–11395.*
Sandrin et al. 1993. Transplantation Proceedings, 25(5): 2917–2918.*
Vaughan et al. 1993. Transplantation Proceedings, 25(5): 2919–2920.*
Stryer 1988 in "Biochemistry", Thrid Edition, W.H. Freemann and Co., N.Y. pp. 263,331–348 and 773–778.*
Platt et al. 1990. Transplantation 50(5): 817–822.*
Stedman's Medical Dictionary, 24$^{th}$ Ed., 1982 Williams and Wilkins, Baltimore, p. 944.*
Van Brunt, 1988. Biotechnology 6(10):1149–1154.*
Wall et al. 1992. Journal of Cellular Biochemistry 49:113–120.*
Shulman et al. 1990. Molecular and Cellular Biology 10(9): 4466–4472.*
Brinster et al. Proc. Natl Acad Sci, USA. 86:7087–7091.*
Cairns et al. 1991. Immunology Letters 29:167–170.*
Alexandre, G.P.J., et al., "Present Experiences in a Series of 26 ABO–Incompatible Living Donor Renal Allografts," Transplantation Proceedings, XIX(6):4538–4542 (1987).
Alexandre, G.P.J., et al., "Plasmapheresis and Splenectomy in Experimental Renal Xenotransplantation", *Material and Methods*, 27:259–266 (1991).
Anderson, E., "Blood Groups in Pigs", *Civil Aeromed In*, 207–225 (1993).
Bach, E.H., et al., "Accommodation—The Role of Natural Antibody and Complement in Discordant Xenograft Rejection", *Accommodation in Other Systems*, 82–91, 97–99 (1991).
Bannett, A.D., et al., "Experiences With Known ABO–Mismatched Renal Transplants", Transplantation Proceedings, XIX(6):4543–4546 (1987).
Bensinger, W.I., et al., "ABO–Incompatible Marrow Transplants", 33(4):427–429 (1982).

(List continued on next page.)

*Primary Examiner*—Jill D. Martin
(74) *Attorney, Agent, or Firm*—Holland & Knight LLP

(57) ABSTRACT

Methods to manipulate animals such as pigs, and the animals and tissues thereby derived, to reduce their immunogenicity following implantation into humans, are described. These methods are based on the discovery that certain carbohydrate structures on pig tissues, which require expression of the gene encoding the α 1→3 galactosyl transferase enzyme, are targets for natural preformed antibodies of humans and elicit further antibody production in humans, while other carbohydrate structures do not or do so in a reduced amount. In the preferred embodiment, animals are produced by homologous recombination of the gene encoding α 1→3 galactosyl transferase in embryonic stem cells or by microinjection into embryos of sequences eliminating or decreasing expression of α 1→3 galactosyl transferase. In alternative embodiments, animals are produced having reduced amounts of α 1→3 galactosyl epitopes or epitopes which are masked by sialylation or fucosylation.

18 Claims, 7 Drawing Sheets

OTHER PUBLICATIONS

Block, K., et al., "Specificity of Binding of a Strain of Uropathogenic *Escherichia coli* to Galα1→4GaL–containing Glycosphingolipids", *The Journal of Biological Chemistry*, 8545–8551 (1985).

Capecchi, M.R., "Altering the Genome by Homologous Recombination", *Science*, 244:1288–1292 (1989).

Cooper, D.K.C., et al., "A Novel Approach to 'Neutralization' of Preformed Antibodies: Cardiac Allotransplantation Across the ABO Blood Group Barrier as a Paradigm of Discordant Transplantation", Transplantation Proceedings, 24(2):566–571 (1992).

Cooper, D.K.C., et al., "The Pig as Potential Organ Donor for Man", *Nonimmunological Considerations*, 481–500 (1991).

Cooper, D.K.C., "Clinical Survey of Heart Transplantation Between ABO Blood Group—Incompatible Recipients and Donors", *The Journal of Heart Transplantation*, 9(4):376–381 (1990).

Cooper, D.K.C., et al., "Effects of Cyclosporine and Antibody Adsorption on Pig Cardiac Xenograft Survival in the Baboon", *The Journal of Heart Transplantation*, 7(3):238–246 (1988).

Cooper, D.K.C., et al., "Experience with Clinical Heart Xenotransplantation", *Xenotransplantation: The Transplantation of Organs and Tissues Between Species*, eds., Springer–Verlag, New York, 541–557 (1991).

Holgersson, J., et al., "Structural Characterization of Non––Acid Glycosphingolipids in Kidneys of Single Blood Group O and A Pigs", *J. Biochem*, 108:766–777 (1990).

Joyner, A.L., et al., "Production of a Mutation in Mouse En–2 Gene by Homologous Recombination in Embryonic Stem Cells", *Nature*, 338:153–156 (1989).

Kirkman, R.L., "Of Swine and Men: Organ Physiology in Different Species", *Xenograft* 25, 125–132 (1989).

Larsen, R.D., et al., "Isolation of a cDNA Encoding a Murine UDP Galactose:β–D–galactosyl–1,4–N–acetyl–Dglucosaminide α–1,3–galactosyltransferase: Expression Cloning by Gene Transfer", *Proc. Natl. Acad. Sci. USA*, 86:8227–8231 (1989).

Lemieux, R.U., "Human Blood Groups and Carbohydrate Chemistry," Chem. Soc. Rev., 7:423–452 (1978).

Mollicone, R., et al., "Immunohistologic Pattern of Type 1 (Le$^a$, Le$^b$) and Type 2 (X, Y, H) Blood Group–Related Antigens in the Human Pyloric and Duodenal Mucosae", *Laboratory Investigation*, 53(2):219–227 (1985).

Murphy, L.A., et al., "Five α–D–Galactopyranosyl–binding Isolectins from *Bandeiraea Simplicifolia* Seeds", *The Journal of Biological Chemistry*, 252(13):4739–4742 (1977).

Oriol, R., "Tissular Expression of ABH and Lewis Antigens in Humans and Animals: Expected Value of Different Animal Models in the Study of ABO–Incompatible Organ Transplant", Transplantation Proceedings, XIX(6):4416–4420 (1987).

Oriol, R., et al., "ABO Antibodies—Serological BEH/Aviour and Immuno–Chemical Characterization", *Journal of Immunogenetics*, 17:279–299 (1990).

Paul, L.C., "Mechanism of Humoral Xenograft Rejection", *Xenotransplantation: The Transplantation of Organs and Tissues Between Species*, eds., Springer–Verlag, New York, 47–67 (1991).

Platt, J.L., et al., "Mechanism of Tissue Injury in Hyperacute Xenograft Rejection", *Xenotransplantation: The Transplantation of Organs and Tissues Between Species*, eds.., Springer–Verlag, New York, 69–79 (1991).

Potter, H., et al., "Enchancer–dependent Expression of Human K Immunoglobulin Genes Introduced Into Mouse Pre–B Lymphocytes by Electroporation", *Proc. Natl. Acad. Sci. USA*, 81:7161–7165 (1984).

Romano, E.L., et al., "Preliminary Human Study of Synthetic Trisaccharide Representing Blood Substance A", Transplantation Proceedings, XIX(6):4475–4478 (1987).

Smith, D.F., et al., "Transfer and Expression of a Murine UDP–Gal:β–D–Gal–α1,3–Galactosyltransferase Gene in Transfected Chinese Hamster Ovary Cells", *The Journal of Biological Chemistry*, 265(1):6225–6234 (1990).

Southern, P.J., et al., "Transformation of Mammalian Cells to Antibiotic Resistance with a Bacterial Gene Under Control of the SV40 Early Region Promoter", *Journal of Molecular and Applied Genetics*, 1:327–341 (1982).

UNOS Update, 9(5):1–45 (1993).

UNOS Annual Report for Jan. 1, 1990—Jun. 30, 1991, "The National Organ Procurement and Transplantation Network," 1–33.

UNOS Update, "Donor Pool Shrinking? Decreasing Vehicular Fatalities, Increases in AIDS Reducing Donor Pool", 9–11, 4143 (1993).

Zimmer, A., et al., "Production of Chimaeric Mice Containing Embryonic Stem (ES) Cells Carrying a Homoeobox Hox 1.1 Allele Mutated by Homologous Recombination", *Nature*, 338:150–153 (1989).

Kayser, H., et al., "Biosynthesis of a Nonphysiological Sialic Acid in Different Rat Organs, using N–Propanoyl–D–Hexosamines as Precursors", *J. Biol. Chem.*, vol. 267(24), p. 16934–16938 Aug. 25, 1992.

Kayser, H., et al., "Incorporation of N–acyl–2–amino–2–deoxyhexoses into glycosphingolipids of the pheochromocytoma cell line PC 12," *FEBS*, vol. 301, No. 2, 137–140 (Apr. 1992).

Lowe, J.B., et al., "Molecular Cloning of a Human Fucosyltransferase Gene that Determines Expression of the Lewis X and VIM–2 epitopes but not ELAM–1–dependent Cell Adhesion, ".

*J. Biol. Chem.*, 266(26), pp. 17467–17477 (Sep. 15, 1991).

* cited by examiner

```
                                  Human genomic DNA  cagcttgtgttctttc
                          aggaatcccagaggataaatgttttgttttcttcttttgtttcaga
                                          Splice acceptor similarity (a)    Y  N  D  H  Y  L  E  E  F  I  T  S  A  N  R
Human protein
Human genomic DNA          TATAATGATCATTACTTGGAGGAGTTCATAACATTCTGCTAATAGGT  538'
                           ||  ||||||||||||||||||||||||||||| || |  ||| ||
Murine cDNA                TACATTGAGCATTACTTAGAAGACTTTCTGGAGTCTGCTGACATGT  538
                    (a)    -  -  I  E  -  -  -  -  D  -  L  E  -  D  M
Murine protein
Bovine protein      (b)    -  -  I  E  -  -  -  -  -  -  L  -  -  -  K
                    (c)

(a)    Y  F  M  V  G  H  K  V  I  F  Y  I  M  V  D  D
Human protein
Human genomic DNA          ACTTCATGGTTGGCCACAAAGTCATATTTTACATCATGGTGGATGA  584'
                           |||||||||||||||||  ||||||||||||| ||||| ||| ||
Murine cDNA                ACTTCATGGTTGGCCATCGGGTCATATTTTACGTCATGATAGACGA  584
                    (a)    -  -  -  -  -  -  R  -  -  -  -  V  -  I  -  -
Murine protein
Bovine protein      (b)    H  -  -  -  -  -  P  -  -  -  -  -  -  -  -  -
                    (c)

```
Human protein      (a)           V   S   K   L   P   F   I   E   L   G   P   L   H   S   F
Human genomic DNA  (b) TGTCTCCAAGCTGCCCGTTTATAGAGCTGGGTCCTCTGCATTCCTTC  630'
                       ||||||||||| |||| |||| ||||||||| ||||||||||||||
Murine cDNA        (c) CACCTCCCGGATGCCTGTCGTGCACCTGAACCCTCTACATTCCTTA  630
Murine protein             T   -   R   M   -   V   V   H   -   -   -   -   -   -   L
Bovine protein             -   -   R   M   -   L   -   -   -   -   R   -   -   -   -

Human protein      (a)           K   M   F   E   V   K   P   E   K   R   W   Q   D   I   S
Human genomic DNA  (b) AAAATGTTTGAGGTCAAGCCAGAGAAGAGGTGGCAAGACATCAGCA  676'
                       || |||||||| || ||||| ||||| |||||||||| ||||||||
Murine cDNA        (c) CAAGTCTTTGAGATCAGGTCTGAGAAGAGGTGGCAGGATATCAGCA  676
Murine protein             Q   V   -   -   I   R   S   -   -   -   -   -   -   -   -
Bovine protein             -   V   -   -   K   I   -   -   -   -   -   -   -   -   -

Human protein      (a)           M   M   R   M   K   I   T   G   E   H   I   L   A   H   I   Q
Human genomic DNA  (b) TGATGCGTATGAAGATCACTGGGGAGCACATCTTGGCCCACATCCA  722'
                       |||||||| |||||||||| |||||||||||| |||||||||||||
Murine cDNA        (c) TGATGCGCATGAAGACCATTGGGGAGCACATCCTGGCCCACATCCA  722
Murine protein             -   -   -   -   -   -   T   I   -   -   -   -   -   -   -
Bovine protein             -   -   -   -   -   -   T   I   -   -   -   V   -   -   -
```

```
                         H  E  V  D  F  L  F  C  M  D  V  D  Q  V  F
Human protein       (a)
Human genomic DNA   (b)  ACACGAGGTCGACTTCCTCTTCTGCATGGATGTGGACCAGGTCTTC  768'
                         ||||||||||||||||||||||||||||||||||||||||||||||
Murine cDNA         (c)  GCACGAGGTCGACTTCCTCTTCTGCATGGACGTGGATCAAGTCTTT  768
Murine protein              —  —  —  —  —  —  —  —  —  —  —  —  —  —  —
Bovine protein              —  —  —  —  —  —  —  —  —  —  —  —  —  —  —

Q  D  H  F  G  V  E  T  L  G  Q  S  V  A  Q
Human protein       (a)
Human genomic DNA   (b)  CAAGACCATTTTGGGGTGGAGACCCTAGGCCAGTCAGTGGCTCAGC  814'
                         ||||||||||||||||||||||||||||||||||||||||||||||
Murine cDNA         (c)  CAAGACAACTTCGGGGTGGAAACTCTCGGGCCAGCTGGTAGCACAGC  814
Murine protein              —  N  —  —  —  —  —  —  L  —  —  —  —  —  —
Bovine protein              —  K  —  —  —  —  —  —  E  —  —  —  —  —  —
```

FIG. 1C

```
                              Premature Termination
                 W   R   Y   K   A   D   P   Y   D   F   T   *   E
Human protein (a)
              (b) L   Q                                                              (AvrII)
              (c) Frameshift
Human genomic DNA TACAGGC TGGCGGGTACAAGGCAGATCCCTATGACTTTACCTAGGA  859'
                  ||||||| ||| |||||||||||||| |||| ||| ||  |||| ||
Murine cDNA       TCCAGGCCTGGTGGTACAAGGCCAGTCCCGAGAAGTTCACCTATGA   860
Murine protein    -   -   A   -   W   -   -   S   -   E   K   -   Y   -
Bovine protein    -   -   A   -   W   -   -   -   -   -   N   -   Y   -

R   W   K   E   S   A   G   Y   I   P   F   G   Q   G
Human protein (a)
              (b)                                                       Frameshift
              (c)
Human genomic DNA GAGGTGGAAAGAGTCAGCAGGATACATTCCATTTGGCCAGGGG AT      904'
                  ||||| || ||  ||| ||  ||| |||||||||||| ||||||  ||
Murine cDNA       GAGGCGGGAACTGTCGGCCGTACATTCCATTCGGAGAGGGGAT        906
Murine protein    -   R   E   L   -   -   A   -   -   -   -   -   E   -   D
Bovine protein    -   R   -   -   -   -   A   -   -   -   -   -   E   -   D
```

```
                           F   Y   Y   H   A   A   I   S   G   G   T   P   I   Q   V
(a) Human protein
(b) Human genomic DNA    TTTTATTACCATGCAGCAGCCATTTCTGGAGGAACACCCATTCAGGTTC    950'
                         ||||  ||||||||  ||||||  ||||||||  |||||||  ||||  ||
(c) Murine cDNA          TTTTACTACCACGCGGCCATTTTTGGAGGAACGCCTACTCACATTC       952
    Murine protein                                 F               T   H   I
    Bovine protein                                 F               T L   N   I   T   Q   E   C   F   K   G   I   L   L   D   K   K
(a) Human protein
(b) Human genomic DNA    TCAACATCACCCAGGAGTGCTTTAAGGGAATCCTCCTGGACAAGAA       996'
                         ||||||||  |||||||||||||||||||||||  |||||||||||
(c) Murine cDNA          TCAACCTCACCCAGGAGTGCTTTAAGGGGATCCTCCAGGACAAGAA       998
    Murine protein                   L       R                           Q
    Bovine protein                   L                                   K N   D   I   E   A   K   W   H   D   E   S   H   L   N   K
(a) Human protein
(b) Human genomic DNA    AAATGACATAGAAGCCAAGTGGCATGATGAGAGCCACCTAAACAAG      1042'
                         |||||||||  |||||||||||||||||||||||||||  |||  ||
(c) Murine cDNA          ACATGACATAGAAGCCCAGTGGCATGATGAGAGCCACCTCAACAAA      1044
    Murine protein           H                   Q
    Bovine protein                               Q
```

FIG. 1F

```
                        Y  F  L  L  N  K  P  S  K  I  L  S  L  K  Y
Human protein       (a)
Human genomic DNA   (b) TATTTCCTTCTCAATAAACCCTCTAAAATCTTATCCCTAAAATACT  1088'
                        ||||||||||||||||||||||||||||||||||||||||||||
Murine cDNA         (c) TACTTCCTTTTCAACAAACCCACTAAAATCCTATCTCCAGAGTATT  1090
Murine protein          -  -  -  F  -  -  -  -  T  -  -  -  P  E  -
Bovine protein          -  -  -  -  -  -  -  -  T  -  -  -  P  E  -

C  W  D  Y  H  I  G  L  P  S  D  I  K  T  V  K
Human protein       (a)
Human genomic DNA   (b) GCTGGGATTATCATATAGGCCTGCCTTCAGATATTAAAACTGTCAA  1134'
                        ||||||||||||||||||||||||||||||||||||||||||||||
Murine cDNA         (c) GCTGGGACTATCAGATAGGCCCTGCCTTCAGATATTAAAAGTGTCAA 1136
Murine protein          -  -  -  -  Q  -  -  -  -  -  -  -  -  S  -  -
Bovine protein          -  -  -  -  H  -  -  -  -  -  A  -  -  L  -  -

*  S  W  Q  T  K  E  Y  N  L  V  R  N  N  V
Human protein       (a)   Premature Termination
Human genomic DNA   (b) GTGATCGTGGCAGACAAAAGAGTATAATTTGGTTAGAAATAATGTC  1180'
                        ||||||||||||||||||||||||||||||||||||||||||||||
Murine cDNA         (c) GGTAGCTTGGCAGACAAAAGAGTATAATTTGGTTAGAAATAATGTC  1182
Murine protein          V  A  -  -  -  -  -  -  -  -  -  -  -  -  -
Bovine protein          M  -  -  -  -  -  -  -  -  -  V  -  -  -  -
```

```
                              (a)
Human protein            (b) Authentic Termination
                          (c)      *
Human genomic DNA     TGACTTCAAATTGTGCCAGTAGATTTCTGAATTTAAGAGAGA   1199'
                      ||||||||||||||||||  ||| | ||  || |  |   |
Murine cDNA           TGACTTCAAATTGTGATGGAAACTTGACACTATTTCTAACCA   1201
Murine protein                *
Bovine protein                *
```

FIG. 1G

GENETICALLY ENGINEERED MAMMALS FOR USE AS ORGAN DONORS

This is a continuation of application Ser. No. 08/049,817 filed on Apr. 20, 1993 now abandoned.

BACKGROUND OF THE INVENTION

The present invention is a genetically-engineered animal such as a pig that is deficient in the α 1→3 galactosyl transferase gene, resulting in non-expression of galactosyl epitopes on its organs and tissues, or in masked expression of galactosyl epitopes on its organs and tissues, and methods for use thereof as a organ donor for humans.

Organ transplantation is now an increasingly successful option open to patients with end-stage disease of vital organs, but is limited by the availability of suitable donors. There is now a worldwide shortage of donor organs, and the number of potential recipients on waiting lists and the period of time that each waits for a suitable organ are both increasing annually, as reported in UNOS Annual Report (1990–1991) and UNOS Update 8, 1, 1992.

At the end of 1990, almost 22,000 patients awaited a solid organ transplant in the USA. One year later, the number had increased to over 25,000, despite the fact that approximately 15,000 organ transplants had been performed during this period. It is unlikely that the availability of human donors will ever be sufficient to match the rapidly increasing number of potential recipients.

One solution to the problem of organ supply would be the use of organs taken from a suitable animal donor. Although the higher non-human primates (apes and monkeys) would provide the closest immunological match for man, there are several factors that make the routine use of these species as organ donors unlikely. These include (i) inadequate numbers, (ii) difficulty and expense of breeding in large numbers, (iii) inadequate size of some organs (e.g., heart) for adult humans, (iv) probability of public concern regarding the use of such species for this purpose, and (v) risk of transfer of serious viral disease.

Attention is, therefore, being directed towards more commonly available mammals that are lower on the phylogenetic scale, in particular, the pig, which has many advantages in this respect, as reported by Kirkman, R. L. Of swine and men: organ physiology in different species. In Hardy, M. D. (ed), *Xenograft* 25, (Elsevier, Amsterdam, New York, Oxford, 1989), pp. 125–132, Cooper, D. K. C., et al. The pig as potential organ donor for man. In *xenotransplantation*. Cooper, K. D. C., Kemp, E., Reemtsma, K., White, D. J. G. (eds.) (Springer, Heidelberg, 1991), pp. 481–500. These include (i) availability in large numbers, (ii) inexpensive to breed and maintain, (iii) suitable size for the smallest or largest of humans, (iv) availability of pathogen-free (gnotobiotic) animals, and (v) considerable similarities of anatomy and physiology with man.

Survival of pig-to-man (or other primate) organ transplants is currently limited, however, by a severe humoral immune response that leads to destruction of the graft within minutes or hours, as reviewed by Cooper, et al. Experience with clinical heart xenotransplantation. In *Xenotransplantation*. Cooper, D. K. C., Kemp, E., Reemtsma, K., White, D. J. G. (eds.). (Springer, Heidelberg, 1991), pp. 541–557, and Cooper, et al. Effects of cyclosporine and antibody adsorption on pig cardiac xenograft survival in the baboon.*J. Heart Transplant* 7:238–246, 1988. The length of the period of survival of organ xenografts decreases with the increase of phylogenetic distance between donor and recipient species.

Xenotransplants between closely-related species can usually survive the initial period of blood perfusion without damage, as do allotransplants. Subsequently, the foreign antigens of the transplanted organ trigger the recipient's immune response and the acute cellular rejection process begins. These xenografts, which behave clinically and histologically like allografts, are termed concordant xenotransplants. Xenografts between phylogenetically distant species follow a clinical course quite different from allotransplants and are termed discordant xenotransplants.

In discordant xenografted organs, vascular rejection occurs within a few minutes of recirculation, with a typical histopathological pattern of endothelial lesions with severe interstitial hemorrhage. This hyperacute rejection is usually irreversible, but can be delayed by removal of the recipient's natural antibodies against the donor tissue. There is now considerable evidence to suggest that this hyperacute rejection is entirely or largely a result of antibody-mediated complement activation through the classical pathway, as reported by Paul, L. C. Mechanism of humoral xenograft rejection. In *Xenotransplantation.* Cooper, D. K. C., Kemp, E., Reemtsma, K., White, D. J. G. (eds.) (Springer, Heidelberg, 1991), pp. 47–67, and Platt, et al. Mechanism of tissue injury in hyperacute xenograft rejection. In *Xenotransplantation,* pp. 69–79, and much attention is being directed towards inhibiting this humoral response.

A similar situation exists with regard to organ allografting across the ABO blood group barrier, from which much of the available information on antibody-mediated hyperacute rejection has been derived, as reviewed by Cooper, D. K. C. A clinical survey of cardiac transplantation between ABO-blood group incompatible recipients and donors. *J. Heart Transplant* 9:376–381, 1990, and Alexandre, et al., Present experiences in a series of 26 ABO-incompatible living donor renal allografts. *Transplant Proc.* 19:4538, 1987. The utilization of synthetic A and/or B blood group trisaccharides (Lemieux, R. U. Human blood groups and carbohydrate chemistry. *Chem. Soc. Rev.* 7:423-, 1978), covalently attached to a solid support in the form of an immunoadsorbent for the extracorporeal depletion of human anti-A and anti-B antibodies, has been shown to facilitate bone marrow and kidney transplantation across the ABO blood group barrier, as shown by Bensinger, et al. ABO-incompatible marrow transplants. *Transplantation* 33:427–429, 1982, and Bannett, et al., Experiences with known ABO-mismatched renal transplants. *Transplant Proc.* 19:4543–4546, 1987, respectively. Prolonged allograft survival even after the return of high titers of anti-A or anti-B antibody, and in the presence of normal levels of complement, has been documented by Alexandre and Bannett, supra, and has subsequently been termed "accommodation" by Bach, et al. Accommodation—the role of natural antibody and complement in discordant xenograft rejection. In *Xenotransplantation,* Cooper, D. K. C., Kemp, E., Reemtsma, K., White, D. J. G. (eds.), Springer, Heidelberg, 1991, pp. 81–99. Using similar methods, shorter periods of accommodation have also been documented following pig-to-baboon heart and kidney xenografting, as reported by Cooper, et al. Effects of cyclosporine and antibody adsorption on pig cardiac xenograft survival in the baboon.*J. Heart Transplant* 7:238, 1988, and Alexandre, et al., Plasmapheresis and splenectomy in experimental renal xenotransplantation. In: Hardy, M. D. (Ed.) *Xenograft* 25. (New York, Elsevier Science Publishers, 1989), p. 259.

An injectable form of the synthetic A and B blood group trisaccharides for the in situ "neutralization" of anti-A and anti-B antibodies (as originally investigated by Romano et al. Preliminary human study of synthetic trisaccharide representing blood substance A *Transplant Proc.* 19:4475–4478, 1987), has been demonstrated to prevent antibody-mediated hyperacute rejection in the baboon and, when combined with standard pharmacologic immunosuppressive therapy, extend experimental ABO-incompatible cardiac allograft survival from a mean of 19 minutes to more than 28 days, with one heart still functioning at almost 2 months, as reported by Cooper, et al., A novel approach to "neutralization" of preformed antibodies: cardiac allotransplantation across the ABO blood group barrier as a paradigm of discordant transplantation. *Transplant Proc.* 24:566–571, 1992.

However, it is clearly impractical to continually infuse the synthetic trisaccharides, or antibodies to the trisaccharides, into a patient, along with the immunosuppressive therapy, over an extended period of time.

As reported in the New York Times Feb. 3, 1993, The DNX Corporation is developing a pig with genes that are intended to mask the immunological markers present in pigs that are used as a source of donor organs for implantation into humans. These pigs are created by microinjection of human DNA into pig embryos. However, the end result is not that the pig genes are eliminated, but that the cells also express human markers.

It is therefore an object of the present invention to provide a long term solution to the problem of alleviating immunorejection of xenotransplants, specifically pig into human, where the rejection is mediated by the glycoprotein structures present on the xenotransplant which are not found in the human.

It is a further object of the present invention to provide genetically engineered tissues which do not express sugars which may elicit an immune, especially a complement-mediated, response following transplantation of an animal organ into a human.

SUMMARY OF THE INVENTION

Methods to manipulate animals, and the animals and organs thereby derived, to reduce their immunogenicity following implantation into humans, are described. These methods are based on the discovery that certain carbohydrate structures on the pig tissues, which require expression of the gene encoding the α 1→3 galactosyl transferase enzyme, are targets for natural preformed antibodies of humans and elicit further antibody production in humans, while other carbohydrate structures do not or do so in a reduced amount. In particular, animals such as pigs are produced by homologous recombination of the gene encoding α 1→3 galactosyl transferase in embryonic stem cells to eliminate expression of the α 1,3 galactosyl transferase gene or by microinjection of cDNA constructs into embryos of sequences inactivating or decreasing expression of α 1→3 galactosyl transferase.

BRIEF DESCRIPTION OF THE DRAWINGS

FIGS. 1A–1G is a comparison of DNA and derived protein sequences of murine α(1,3)-GT cDNA, bovine α(1,3)-GT CDNA, and cloned homologous human genomic sequences, as shown at page 7058 of Larsen, et al., *J. Biol. Chem.* 265(12), 7055–7061 (1990). The nucleotide sequence of an 801-bp segment of pHGT-1 (human genomic DNA) is shown, with the corresponding amino acid sequence derived from the relevant reading frame (human protein, reading frames denoted by a, b and c). The nucleotide sequence is numbered in register with the sequence of the murine α(1,3)-GT cDNA, Sequence ID No. 1, a portion of which is displayed (murine cDNA) below the human DNA sequence. Vertical lines between the murine and human DNA sequences denote nucleotide sequence identity. Human genomic DNA sequences located 5' from bp 492' which exhibit no homology to the murine α(1,3)-GT cDNA, are displayed in lower case letters. A portion of this part of the human sequence which displays strong similarity to the mammalian consensus splice acceptor sequence is double underlined. The predicted amino acid sequences inferred from the nucleotide sequences of the murine α(1,3)-GT cDNA (murine protein) and the bovine α(1,3)-GT cDNA (bovine protein) are indicated below the murine nucleotide sequence. Amino acids within these sequences that are identical to the corresponding human amino acid residue are indicated by a hyphen. The two segments of the human DNA used to generate the polymerase chain reaction amplimers are denoted by the stippled underlining. The AvrII site used to analyze the polymerase chain reaction products is underlined.

DETAILED DESCRIPTION OF THE INVENTION

Working on the hypothesis that those portions of the antigenic targets against which human anti-pig antibodies are directed are also carbohydrate structures, carbohydrate structures present in pig but not human which appear to elicit an immune response against the pig tissues when transplanted into humans have been identified. A method to create pigs, as well as other animals, for use as potential organ and tissue donors has been developed based on this information. This method, and the animals produced using the method, should be effective in achieving successful organ transplantation between these animals and man in a manner similar to that achieved when organ transplantation is performed between donor and recipient of ABO-incompatible allografts.

When pig tissues are implanted into humans, they elicit the production of antibodies against the pig tissues. These antibodies have been isolated and characterized for immunoreaction against specific components or fractions of pig tissues to determine which pig-specific molecules elicit the antibody production, as described below in Example 1.

Numerous carbohydrate structures bound human anti-pig antibodies eluted from one or more pig heart and/or pig kidney transplants. The populations of anti-carbohydrate antibodies varied slightly depending on the pig organ and the individual human serum adsorbed. Four α-galactosyl related molecules (haptens), however, bound all of the human anti-pig kidney antibodies and most of the anti-pig heart antibodies. These four haptens were: (i) α Gal(1→3) β Gal(1→4) β GlcNac (linear B type 2), (ii) α Gal (1→3) β Gal (1→4) β Glc (linear B type 6), (iii) α Gal(1→3) β Gal (B disaccharide), and (iv) α Gal (α-D-galactose). All yielded high optical density (O.D.) results for the samples tested. Significant levels of both IgG and IgM anti-linear B antibodies were detected, although in some preparations, IgG anti-linear B antibodies predominated.

Other carbohydrate haptens were bound by antibodies from individual eluted antibody preparations, including (i) N-acetyl-β-D-glucosaminide (β GlcNac) and other structures containing a terminal β GlcNac, (ii) α-L-Rhamnose and Rhamnose-containing structures, (iii) Forssman disaccharide and Forssman trisaccharide, (iv) A or A-like carbohydrates (namely A disaccharide, A trisaccharide, a variety of A tetrasaccharides and linear A type 6). However, these carbohydrates were not bound by significant levels of antibody from all preparations and were demonstrated not to elicit the most significant immunoreactions, as shown by the data in example 1 below.

The human anti-pig antibody preparations in this study contained primarily IgG anti-linear B, but some preparations contained IgM anti-linear B. Anti-pig antibodies can be adsorbed from human plasma by passing the plasma through a column of one or more of the specific linear α-Galactosyl structures. Moreover, the addition of the specific carbohydrate to human serum also appears to inhibit or "neutralize" the destructive effect, wholly or in part, of the serum on pig kidney and endothelial cell lines.

The adsorption or "neutralization" of such anti-pig antibodies by a specific carbohydrate or combination of carbohydrates, utilizing one (or a combination) of the above two techniques, should prevent the hyperacute rejection that occurs when xenotransplantation is carried out using a discordant donor in man, based on the survival of ABO-incompatible cardiac allografts in hyperimmunized baboons from a mean of 19 minutes in untreated animals to several weeks in recipients receiving a continuous intravenous infusion of A or B synthetic hapten (for periods less than 19 days) and long-term pharmacologic immunosuppressive therapy, as reported by Cooper, et al., 1992.

Based on these studies, production of pig-specific carbohydrate structures eliciting an immune response is due to expression in pigs of the enzyme α 1→3 galactosyl transferase. A means is described herein of genetically engineering animals that do not express the α-galactosyl epitope on their cells, or in which the epitope is reduced in frequency or masked from the immune response, making xenotransplantation possible without the need for prior removal or "neutralization" of the human anti-galactosyl antibodies.

To prevent expression of the α 1→3 galactosyl transferase, the gene is deleted, interrupted, or replaced, either within the coding region or within the regulatory sequences, so that enzyme is not produced. This is generally accomplished by manipulation of animal embryos followed by implantation of the embryos in a surrogate mother. The embryos can be manipulated directly, by injection of genetic material into the embryo by microinjection or by vectors such as retroviral vectors, or indirectly, by manipulation of embryonic stem cells. The latter methodology is particularly useful in the case where the end result that is desired is to completely prevent expression of an active enzyme. In some cases, however, it may simply be that one wants to decrease expression, where there is a role of the protein encoded by the gene that is essential to viability or health of the animal and the optimum results are achieved by suppression, rather than eliminating gene expression, or one may want to introduce a gene for an enzyme which can "cap" or mask the α 1→3 galactosyl epitopes. Suppression can be achieved by introduction of pig antisense to the α 1→ galactosyl transferase gene.

Genes encoding a galactosyl transferase from species other than, but related to, pig, have been identified and can be used with standard techniques, for example, hybridization under stringent conditions or polymerase chain reaction, to obtain the pig α galactosyl transferase gene. Accordingly, the most preferred method at this time is to use microinjection methodology to eliminate the gene from the animals by homologous recombination of the gene.

"Isolation of a CDNA encoding a murine UDP:galactose:β-D-galactosyl-1,4-N-acetyl-D-glucosaminide α-1,3-galactosyltransferase: Expression cloning by gene transfer", Larsen, et al., *Proc. Natl. Acad. Sci. USA* 86, 8227–8231 (1989), the teachings of which are incorporated herein, describes how to isolate cloned cDNA sequences that determine expression of cell surface oligosaccharide structures and their cognate glycosyltransferases. See also Smith, et al., "Transfer and Expression of a Murine UDP-Gal:β-D-Gal-α1,3-Galactosyltransferase Gene in Transfected Chinese Hamster Ovary Cells" *J. Biol. Chem.* 265(11), 6225–6234 (1990). They identified a cDNA, Sequence ID No. 1, containing a single long open reading frame that predicts a 394 amino acid protein, Sequence ID No. 2, having a topology similar to other mammalian glycosyltransferases and which could be inserted into COS cells not expressing (α1→3)GT and result in formation of Gal(α1→3)Gal(β1→4)GlcNAc on the cell surfaces. Subsequent studies by Larsen, et al., "Frameshift and Nonsense Mutations in a Human Genomic Sequence Homologous to a Murine UDP-Gal:β-D-Gal(1,4)-D-GlcNAc α(1,3)-Galactosyltransferase cDNA" *J. Biol. Chem.* 265(12), 7055–7061 (1990), demonstrates that the human gene corresponding to the murine gene for the galactosyltransferase is defective and therefore cannot determine expression of Galα1→3Gal epitopes on human cells. The information used in these publications can be used to obtain a genomic DNA clone to delete or inactivate the corresponding galactosyltransferase gene in pigs and other animals using microinjection of the DNA to inactivate or delete the animal galactosyltransferase responsible for expression of structures on the cells which elicit the major immunorejection of the cells when implanted into humans. A comparison of DNA and derived protein sequences of murine α(1,3)-GT cDNA, bovine α(1,3)-GT cDNA, and cloned homologous human genomic sequences, as shown at page 7058 of Larsen, et al. (1990), is shown in FIGS. 1A–1G.

The murine cDNA sequence (Sequence ID No. 1) is as follows:

```
CCTTCCCTTGTAGACTCTTCTTGGAATGAGAAGTACCGATTCTGCTGAAGACCTCGCGCTCTCAG

GCTCTGGGAGTTGGAACCCTGTACCTTCCTTTCCTCTGCTGAGCCCTGCCTCCTTAGGCAGGCCA

GAGCTCGACAGAACTCGGTTGCTTTGCTGTTTGCTTTGGAGGGAACACAGCTGACGATGAGGCTG

ACTTTGAACTCAAGAGATCTGCTTACCCCAGTCTCCTGGAATTAAAGGCCTGTACTACATTTGCC

TGGACCTAAGATTTTC (non-coding region)

ATGATCACTATGCTTCAAGATCTCCATGTCAACAAGATCTCCATGTCAAGATCCAAGTCAGAAAC

AAGTCTTCCATCCTCAAGATCTGGATCACAGGAGAAAATAATGAATGTCAAGGGAAAAGTAATCC
```

```
                            -continued
TGTTGATGCTGATTGTCTCAACCGTGGTTGTCGTGTTTTGGGAATATGTCAACAGAATTCCAGAG

GTTGGTGAGAACAGATGGCAGAAGGACTGGTGGTTCCCAAGCTGGTTTAAAAATGGGACCCACAG

TTATCAAGAAGACAACGTAGAAGGACGGAGAGAAAAGGGTAGAAATGGAGATCGCATTGAAGAGC

CTCAGCTATGGGACTGGTTCAATCCAAAGAACCGCCCGGATGTTTTGACAGTGACCCCGTGGAAG

GCGCCGATTGTGTGGGAAGGCACTTATGACACAGCTCTGCTGGAAAAGTACTACGCCACACAGAA

ACTCACTGTGGGGCTGACAGTGTTTGCTGTGGGAAAGTACATTGAGCATTACTTAGAAGACTTTC

TGGAGTCTGCTGACATGTACTTCATGGTTGGCCATCGGGTCATATTTTACGTCATGATAGACGAC

ACCTCCCGGATGCCTGTCGTGCACCTGAACCCTCTACATTCCTTACAAGTCTTTGAGATCAGGTC

TGAGAAGAGGTGGCAGGATATCAGCATGATGCGCATGAAGACCATTGGGGAGCACATCCTGGCCC

ACATCCAGCACGAGGTCGACTTCCTCTTCTGCATGGACGTGGATCAAGTCTTTCAAGACAACTTC

GGGGTGGAAACTCTGGGCCAGCTGGTAGCACAGCTCCAGGCCTGGTGGTACAAGGCCAGTCCCGA

GAAGTTCACCTATGAGAGGCGGGAACTGTCGGCCGCGTACATTCCATTCGGAGAGGGGGATTTTT

ACTACCACGCGGCCATTTTTGGAGGAACGCCTACTCACATTCTCAACCTCACCAGGGAGTGCTTT

AAGGGGATCCTCCAGGACAAGAAACATGACATAGAAGCCCAGTGGCATGATGAGAGCCACCTCAA

CAAATACTTCCTTTTCAACAAACCCACTAAAATCCTATCTCCAGAGTATTGCTGGGACTATCAGA

TAGGCCTGCCTTCAGATATTAAAAGTGTCAAGGTAGCTTGGCAGACAAAAGAGTATAATTTGGTT

AGAAATAATGTCT (coding region)

GACTTCAAATTGTGATGGAAACTTGACACTATTTCTAACCA (non-coding region)
```

Sequence ID No. 2 is the amino acid sequence:

```
M I T M L Q D L H V N K I S M S R S K S E T S L P S S R S G S Q E
K I M N V K G K VILLMLIVSTVVVVFWEYVN R I P E V
G E N R W Q K D W W F P S W F K N G T H S Y Q E D N V E G R R E K
G R N G D R I E E P Q L W D W F N P K N R P D V L T V T P W K A P
I V W E G T Y D T A L L E K Y Y A T Q K L T V G L T V F A V G K Y
I E H Y L E D F L E S A D M Y F M V G H R V I F Y V M I D D T S R
M P V V H L N P L H S L Q V F E I R S E K R W Q D I S M M R M K T
I G E H I L A H I Q H E V D F L F C M D V D Q V F Q D N F G V E T
L G Q L V A Q L Q A W W Y K A S P E K F T Y E R R E L S A A Y I P
F G E G D F Y Y H A A I F G G T P T H I L N L T R E C F K G I L Q
D K K H D I E A Q W H D E S H L N K Y F L F N K P T K I L S P E Y
C W D Y Q I G L P S D I K S V K V A W Q T K E Y N L V R N N V *
```

Construction of Transgenic Animals

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats.

Microinjection Procedures

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art.

Transgenic Animals

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Embryonic Stem (ES) Cell Methods

Introduction of cDNA into ES Cells

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach,* ed. E. J. Robertson, (IRL Press 1987), the teachings of which are incorporated herein. Selection of the desired clone of transgene-containing ES cells is accomplished through one of several means. In cases involving sequence specific gene integration, a nucleic acid sequence for recombination with the α(1→3) galactosyl transferase gene or sequences for controlling expression thereof is co-precipitated with a gene encoding a marker such as neomycin resistance. Transfection is carried out by one of several methods described in detail in Lovell-Badge, in *Teratocarcinomas and embryonic stem cells, a practical approach,* ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, a number of ES cells, for example, $0.5 \times 10^6$, are plated into tissue culture dishes and transfected with a mixture of the linearized nucleic acid sequence and 1 mg of pSV2neo DNA (Southern and Berg, *J. Mol. Appl. Gen.* 1:327–341 (1982)) precipitated in the presence of 50 mg lipofectin in a final volume of 100 $\mu$l. The cells are fed with selection medium containing 10% fetal bovine serum in DMEM supplemented with an antibiotic such as G418 (between 200 and 500 $\mu$g/ml). Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989)). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES Cell Injection

Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10–20 ES cells are injected into blastocysts using a glass microneedle with an internal diameter of approximately 20 $\mu$m.

Transfer of Embryos to Pseudopregnant Females

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Transgenic Animals.

Samples (1–2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding and used as the donors for tissue removal and implantation using standard techniques for implantation into humans.

Insertion or modification of the aenomic DNA encoding α 1→3 galactosyltransferase or the 1→3 galactosyl structures.

These manipulations are performed by insertion of cDNA or genomic DNA into the embryo using microinjection or other techniques known to those skilled in the art such as electroporation. The DNA is selected on the basis of the purpose for which it is intended: to inactivate the gene encoding an enzyme such as the α 1→3 galactosyltransferase. The enzyme encoding gene can be modified by homologous recombination with a DNA for a defective enzyme, such as one containing within the coding sequence an antibiotic marker, which can then be used for selection purposes.

The gene encoding an α 1→3 galactosyltransferase is described by Larsen, et al., 1990. Frameshift and Nonsense Mutations in a Human Genomic Sequence Homologous to a Murine UDP-Gal:β-D-Gal(1,4)-D-GlcNAc α(1,3)-Galactosyltransferase cDNA *J. Biol. Chem.* 265(12), 7055–7061, the teachings of which are incorporated herein.

Alternative methodologies to produce animals with altered expression of α 1→3 galactosyl transferase.

The DNA encoding another enzyme for modification of the sugar structures, such as a sialylase, can also be inserted into the embryo where it is incorporated into the animal's chromosomes and expressed to modify or mask the immunoreactivity of the α-galactosyl structures on the cell surfaces.

Although not preferred, in some cases it may be equally useful to alter expression of α 1→3 galactosyl transferase in the pigs using techniques other than genetic engineering. For example, pigs can be selected for decreased expression of α 1→3 galactosyl transferase and bred by standard techniques to produce animals that are deficient in this enzyme. It is routine to screen animals both for the presence of, and expression of, enzymes, as well as defined epitopes on the tissues, although prior to this disclosure one would not have been motivated to screen for expression of α 1→3 galactosyl transferase in transgenic animals for use as organ donors.

The same effect may also be achieved through the use of retroviral vectors, especially tissue specific vectors, which carry nucleic acid sequences, such as antisense sequences, resulting in decreased expression of the gene encoding α 1→3 galactosyl transferase.

Methods for Masking expression of α-galactosyl epitopes.

It is possible not only to decrease or completely inhibit expression of the α-galactosyl epitopes on the animal tissues, but also to mask them by attaching another carbohydrate to the epitopes to mask them from the immune response following transplantation. This can be accomplished by introduction into the animal of a gene encoding an enzyme that "caps" the α-galactosyl epitopes or by the use of an introduced enzyme plus manipulation of substrate feeding to cap the epitopes.

It has been hypothesized that the lack of α-galactosyl epitopes in man and Old World monkeys is the result of diminishing activity of one enzyme, the α(1→3) galactosyltransferase. The membrane glycoproteins of human cells are usually sialylated by sialyltransferase. The diversity in carbohydrate structure presumably arises from a multiplicity of synthetic enzymes in different species or different cells. Switching galactosyltransferase with fucosyl or sialyltransferase in animal cells should result in the expression of fucose or sialic acid in their antigen epitopes.

A human α-1,3 fucosyltransferase has been cloned by Koszdin and Bowen, 1992 The Cloning and Expression of a Human α-1,3 Fucosyltransferase Capable of Forming the E-Selectin Ligand *Biochem. Biophys. Res. Comm.* 187(1), 152–157; and Lowe, et al., 1991 Molecular Cloning of a Human Fucosyltransferase Gene That Determines Expression of the Lewis x and VIM-2 Epitopes but Not ELAM-1-dependent Cell Adhesion, *J. Biol. Chem.* 266(26), 17467–17477, the teachings of which are incorporated herein. Human α(1-3)fucosyltransferase was transfected into mammalian cells, which resulted in the expression of Lewis X and sialyl Lewis carbohydrate structures in the cell membrane.

Kayser, et al., 1992 Incorporation of N-acyl-2-amino-2-deoxy-hexoses into glycosphingolipids of the pheochromocytoma cell line PC 12, *FEBS* 301(2), 137–140; and Kayser, et al., 1992 Biosynthesis of a Nonphysiological Sialic Acid in Different Rat Organs, using N-Propanoyl-D-hexosamines as Precursors, *J. Biol. Chem.* 267(24), 16934–16938, have successfully modified the N-acetyl neuraminic acid which is normally present in rat tissues by the in vivo administration of chemically synthesized N-propanoyl precursors. Rat cells are able to take up N-acetyl D-mannosamine or N-propanoyl D-glucosamine as precursors, and the presence of sialyltransferase in rat cells can incorporate these precursors into glycolipids and glycoproteins, which are expressed in the cell membrane.

It therefore should be possible to inject galactosyl analogues into animals such as the pig where they will compete with the natural substrate to be transferred to glycoproteins. Even a slight change of carbohydrate epitope could reduce antibody binding. It is preferable to modify the epitope to a carbohydrate that is present in the human subject so that antibodies against this carbohydrate are not present in the human recipient of the animal organ. If it is modified to any other carbohydrate, then antibodies to this carbohydrate might develop if the carbohydrate is not naturally occurring in the human subject.

Although not preferred, this same methodology can also be used to inhibit or decrease expression of other carbohydrate structures on non-human animal tissues, to further enhance compatibility, including structures such as (i) N-acetyl-β-D-glucosaminide (β GlcNac) and other structures containing a terminal β GlcNac, (ii) α-L-Rhamnose and Rhamnose-containing structures, (iii) Forssman disaccharide and Forssman trisaccharide, and (iv) A or A-like carbohydrates (A disaccharide, A trisaccharide, a variety of A tetrasaccharides and linear A type 6).

Once the animals are produced, tissues, including skin, heart, livers, kidneys, lung, pancreas, small bowel, and components thereof are harvested and implanted as known by those skilled in the art of transplantation.

EXAMPLE 1

Demonstration of Importance of α-Gal in Eliciting Immune Mediated Rejection of Xenotransplants From Pigs Into Humans Pig tissues were screened by immunofluorescence with lectins, monoclonal antibodies and human natural antibodies for the presence of carbohydrate antigens which may be potential targets for hyperacute vascular rejection in pig-to-man xenotransplantation. The unfucosylated monomorph linear B-antigen was found at the surface of all porcine vascular endothelial cells. This pig linear-B antigen reacts strongly with the anti-α Gal isolectin $B_4$ from *Griffonia simplicifolia* 1 and with human natural anti-α Gal antibodies specifically purified by affinity chromatography on synthetic oligosaccharides containing the terminal non-reducing α Gal1→3β Gal-R disaccharide. This antigenic activity is destroyed by treatment of pig tissues with α-galactosidase. The localization of this linear-B epitope on vascular endothelium and its reactivity with natural human anti-α Gal antibodies suggest that it may play a major role in the hyperacute vascular rejection of pig-to-man organ xenografts. Unlike pigs, humans express the fucosylated polymorphic ABH histo-blood group antigens on vascular endothelium.

Epithelial cells of pig renal proximal convoluted tubules, respiratory epithelium, pancreatic ducts and epidermis also express the linear-B antigen, but they are less likely to trigger a hyperacute vascular rejection because they are not directly exposed to the blood.

The genetically defined pig A+/A– system controls the expression of A and H antigens in pig epithelial cells from renal distal and collecting tubules, biliary ducts, pancreatic ducts, large bronchi and digestive mucosa. The pig A antigen may trigger an immune response in human O or B recipients if they are transplanted with organs from A+ pigs, but the pig A antigen is probably not involved in the hyperacute vascular rejection of a xenograft because it is not expressed on vascular endothelium.

Materials and Methods

Pig tissues:

Pigs do not express the ABH blood group antigens as constitutive glycoproteins of the erythrocyte membrane, as do humans. However, there are genetically defined A+ and A– pigs, which can be identified by hemagglutination with some strong anti-A reagents. The A+ or "A like" pigs have a circulating A glycosphingolipid which is passively adsorbed at the surface of erythrocytes and leukocytes, while the A– or "O like" pigs have a circulating H glycosphingolipid which is passively adsorbed on the same cells, as reported by Oriol R. Tissular expression of ABH and Lewis antigens in humans and animals: Expected value of different animal models in the study of ABO-incompatible organ transplants. *Transplant Proc.* 1987 19:4416–4420. The serum of A– pigs can agglutinate red cells of A+ pigs, but the reaction is weak and can take a long time to be completed, as discussed by Andresen, "Blood groups in pigs" *Ann. N.Y. Acad. Sci.* 97,205–225 (1962).

Two A+ and two A− healthy Yorkshire pigs from a specific pathogen-free herd at the Oklahoma State University were selected serologically. Tissue samples of myocardium, aorta, kidney, liver, pancreas, lung, intestine and skin were divided into two. One sample was maintained frozen at −80° C. for cryostat sections, and the second was fixed in formalin 10% (SIGMA, USA) and embedded in paraffin wax by routine histological techniques.

Lectins. Tetramethyl rhodamine isothiocyanate (TRIT)-labelled, *Ulex europaeus* agglutinin 1 staining H-type-2 ($\alpha$ Fuc1→2$\beta$Gal1→4$\beta$GlcNAc) and Le$^y$ ($\alpha$ Fuc1→2$\beta$Gal1→4($\alpha$Fuc1→3)BGlcNAc), *Griffonia simplicifolia* lectin 1 staining terminal $\alpha$Gal and $\alpha$GalNAc, and fluorescein isothiocyanate (FITC)-labelled *Arachis hypogaea* lectin (peanut agglutinin, PNA) staining terminal $\beta$Gal1→3a GalNAc disaccharide>$\alpha$ or $\beta$Gal were obtained from Vector Laboratories (Burlingame, Calif., USA). FITC-labelled *Helix pomatia* (anti-Forssmann>anti-A>$\alpha$Gal), and isolectins A$_4$ ($\alpha$GalNAc>$\alpha$Gal) and B$_4$ (specific for $\alpha$Gal) from *Griffonia simplicifolia* lectin 1 were obtained from E-Y (San Mateo, Calif., USA).

Monoclonal antibodies. Nineteen anti-A (001, 002, 005, 006, 008, 009, 012, 013, 014, 016, 018, 020, 021, 022, 048, 049, 050, 052, 053), seventeen anti-B (025, 026, 028, 031, 032, 033, 034, 035, 036, 037, 040, 041, 042, 043, 044, 046, 047), and four anti-II-type-2 (058, 059, 063 and 064) monoclonal reagents were obtained from the Second International Workshop on Monoclonal Antibodies against Human Red Blood cells and Related Antigens, Lund, Sweden, 1990 (Oriol, et al., "ABO antibodies-serological behaviour and immuno-chemical characterization" *J. Immunogenet.* 17, 279–299 (1990). Anti-Le$^x$ (80H5 and 82H5) were obtained from Chembiomed Ltd. (Alberta Research Council, Edmonton, Canada).

*Polyclonal hyperimmune animal antibodies.* Polyclonal anti-H (SupH) antibodies, described by Mollicone, et al., "Immunohistologic pattern of type 1 (Le$^a$,Le$^b$) and type 2 (X,Y,H) blood group-related antigens in the human pyloric and duodenal mucosae" *Lab. Invest.* 53, 219–227 (1985), were obtained from the serum of a goat hyperimmunized with human saliva from a blood group O Le(a−b−) individual, salivary secretor of H antigen. Specific anti-H antibodies were purified from this serum by affinity chromatography on synthetic H-type-2 immunoadsorbent (Chembiomed Ltd., Alberta Research Council, Edmonton, Canada). The purified anti-H reagent recognized H-type-1, H-type-2, H-type-3, H-type-4, H-type-5 and H-type-6 synthetic oligosaccharides.

Polyclonal anti-H-type-1 (gift of S. Henry, Auckland Blood Transfusion Center, New Zealand) was obtained from the serum of rabbits immunized with human saliva of blood group O Le (a−g−) salivary secretor individuals. Anti-H-type-2 activity of this serum was removed by adsorption with H-type-2 immunoadsorbent and the specific anti-H-type-1 antibodies were then purified by affinity chromatography on the H-type-1 immunoadsorbent (Chembiomed Ltd., Alberta Research Council, Edmonton, Canada). This purified anti-H-type-1 reagent cross-reacted with the type 1 Le$^b$ synthetic oligosaccharides, but did not cross-react with H-type-2 structures.

Purification of natural anti-$\alpha$ Gal human antibodies. Five different fractions of human anti-$\alpha$ Gal antibodies were obtained by affinity chromatography of normal human serum on solid immunoadsorbents made with five structurally related synthetic oligosaccharides, described by Lemieux "Human blood groups and carbohydrate chemistry" *Chem. Soc. Rev.* 7, 423–452 (1978), covalently coupled through the aliphatic linking arm R=(CH$_2$)$_8$COOCH$_3$ to a silica matrix (Synsorb™ from Chembiomed Ltd.). The structures of the synthetic oligosaccharide coupled to the immunoadsorbent were (i) the terminal monosaccharide of the linear-B epitope $\alpha$-Gal-R, (ii) the terminal disaccharide of the linear-B epitope $\alpha$Gal1→3$\beta$Gal-R, (iii) the trisaccharide linear-B-type-2 epitope $\alpha$Gal1→3$\beta$GlcNAc-R, (iv) the trisaccharide linear-B-type-6 or deacetylated linear-B-type-2 $\alpha$Gal1→3$\beta$Gal1→4$\beta$Glc-R and (v) the terminal disaccharide of the P$_1$ red cell antigen $\alpha$Gal1→4$\beta$Gal-R, that is also a receptor for a uropathogenic *Escherichia coli*, as reported by Bock, et al., "Specificity of binding of a strain of uropathogenic *Escherichia coli* to Gal$\alpha$ 1-4Gal-containing glycosphingolipids" *J. Biol. Chem.* 260, 8545–8551 (1985), and has the second galactose linked 1→4 instead of the 1→3 linkage of the linear-B. This last oligosaccharide structure has been found in several pig glycolipids, as reported by Holgersson, et al., "Structural characterization of non-acid glycosphingolipids in kidneys of single blood group O and A pigs" *J. Biochem.* 108, 766–777 (1990).

Small columns (0.5 cm diameter×10 cm height) were packed with 1 g of each immunoadsorbent. Aliquots of 3 ml of a pool of normal human serum were adsorbed onto each column, and the columns were washed with phosphate buffered saline (PBS) until the OD at 280 nm of the eluate was<0.005. Then the adsorbed antibodies were eluted with NH$_4$OH 1% (pH 11) and dialyzed against PBS. The final yield of protein was 0.6 mg for the monosaccharide $\alpha$-galactose immunoadsorbent and about 1 mg for the di and trisaccharide immunoadsorbents.

Secondary antibodies. Affinity purified, FITC-labelled sheep anti-mouse and anti-rabbit Ig were obtained from Pasteur Diagnostics (Marnes la Coquette, France). FITC-labelled Fab fragment of affinity purified anti-human Ig was obtained from Biosys (Compiegne, France). FITC- labelled, affinity purified, pig anti-goat Ig was obtained from E-Y (San Mateo, Calif., USA).

Glycosidases. $\alpha$-galactosidase EC 3.2.1.22 from green coffee beans, $\beta$-galactosidase EC 3.2.1.23 from *Escherichia coli*, $\alpha$-fucosidase EC 3.2.1.51 from beef kidney and neuraminidase EC 3.2.1.18 from *Vibrio cholera*, were obtained from Boehringer (Mannheim, Germany). Enzymatic digestions of the histological cuts were performed, at the optimum pH for each enzyme, by 24 h incubation ($\alpha$-fucosidase) or 2 h incubation (all of the others) in a closed wet chamber at 37° C. After digestion, tissues were washed and studied by immunofluorescence.

Immunofluorescence. Direct, indirect and polychromatic immunofluorescence were carried out on both cryostat and deparaffinated tissue sections.

For direct immunofluorescence, slides were incubated for 30 min in a wet chamber with the optimal dilution of the FITC or TRITC-labelled lectins.

Indirect immunofluorescence was performed under similar conditions. Both incubations with primary antibodies and the corresponding FITC-labelled anti-Ig secondary antibodies were of 30 min duration.

Green and red polychromatic fluorescence was performed either with simultaneous 30 min incubation with two lectins, one labelled with FITC and the other with TRITC, or with a primary antibody revealed with a mixture of the corresponding FITC-labelled secondary anti-Ig antibody and a TRITC-labelled lectin. After staining, slides were washed, and mounted under coverslides with Vectashield™ (Vector Laboratories, Burlingame, Calif., USA).

The immunofluorescence results were observed on a Leitz fluorescence SM-Lux microscope equipped with a lamp source of 200 W HBO, a Ploemopak illuminator and a dual band filter set allowing simultaneous visualization of green and red fluorescence (Omega Optical, Brattleboro, Vt., USA). Pictures were taken with a Leitz Photoautomat MPS50 on Fujichrome 400 ASA, 24×36 mm films.

Results

Vascular endothelium and heart muscle.

Both cryostat and deparaffinated sections gave the same fluorescence pattern of reactivity in all pigs. The purified human anti-linear-B reagents were positive on all vascular endothelial cells from capillaries to aorta, irrespective of the size of the blood vessel (Tables 1 and 2).

TABLE 1

Immunofluorescent staining of tissues from A+ pigs with: Human anti-αGal (αGal); *Griffonia simplicifolia* 1 isolectin $B_4$ (GSI); anti-B (B); *Helix pomatia* (HPA); anti-A (A); anti-H (SupH); *Ulex europaeus* 1 (UEA); anti-H-type-2 (Ht2); anti-H-type-1 (Ht1); peanut agglutinin (PNA) and anti-$Le^X$ ($Le^X$).

| Tissue | αGal | GSI | B | HPA | A | SupH | UEA | Ht2 | Ht1 | PNA | $Le^X$ |
|---|---|---|---|---|---|---|---|---|---|---|---|
| Vascular endothelium | +++ | +++ | − | + | − | − | − | − | − | − | − |
| Heart muscle | − | − | − | − | − | − | − | − | − | − | − |
| Kidney | | | | | | | | | | | |
| glomer, basal mem. | − | − | − | − | − | − | − | − | − | +++ | − |
| proximal tubules | +++ | +++ | ++ | + | − | − | − | − | − | − | − |
| thin Henle limbs | + | + | − | − | − | − | − | − | − | − | − |
| large henle limbs | − | − | − | ++ | ++ | − | − | − | − | ++ | − |
| distal tubules | − | − | − | +++ | +++ | ± | ± | ± | − | ++ | +++* |
| collecting ducts | ± | + | − | ++ | ++ | ± | − | − | − | ++ | − |
| calyces | ± | + | − | ++ | +++ | − | ± | − | − | + | − |
| urinary epithelium | ± | + | − | ++ | +++ | − | ± | ± | − | + | − |
| Liver | | | | | | | | | | | |
| duct epithelium | − | − | − | ++ | +++ | ± | − | − | + | + | − |
| hepatocytes | − | + | − | − | − | − | − | − | − | − | − |
| Pancreas | | | | | | | | | | | |
| duct epithelium | + | + | − | +++ | + | ± | + | + | + | + | − |
| Langerhans islets | − | − | − | − | − | ++ | − | − | + | ++ | − |
| Lung | | | | | | | | | | | |
| bronchus epithelium | − | − | − | ++ | +++ | ± | ± | − | ± | + | − |
| seromucous glands | + | + | − | ++ | +++ | − | − | − | − | +++ | − |
| bronchiole | +++ | +++ | + | + | + | − | − | − | − | + | − |
| alveoli | ++ | ++ | ++ | ± | − | − | − | − | − | − | − |
| Small intestine | | | | | | | | | | | |
| brush border | − | − | − | ++ | +++ | ++ | − | − | − | − | − |
| goblet cells | − | − | − | +++ | +++ | +++ | ++ | − | − | + | − |
| Skin | | | | | | | | | | | |
| stratum granulosum | − | − | − | + | − | ++ | + | + | − | ++ | − |
| stratum spinosuim | + | + | − | + | − | ++ | − | − | − | ++ | − |
| hair follicles | − | − | − | ± | − | ++ | − | − | ± | + | − |
| apocrine glands | − | − | − | ++ | − | +++ | +++ | + | ± | + | − |

*Only the macula densa in front of the glomerular vascular pole was positive.

TABLE 2

Immunofluorescent staining of tissues from A− pigs with: Human anti-αGal (αGal); *Griffonia simplicifolia* 1 isolectin $B_4$ (GSI); anti-B (B); *Helix pomatia* (HPA); anti-A (A); anti-H (SupH); *Ulex europaeus* 1 (UEA); anti-H-type-2 (Ht2); anti-H-type-1 (Ht1); peanut agglutinin (PNA) and anti-$Le^X$ ($Le^X$).

| Tissue | αGal | GSI | B | HPA | A | SupH | UEA | Ht2 | Ht1 | PNA | $Le^X$ |
|---|---|---|---|---|---|---|---|---|---|---|---|
| Vascular endothelium | +++ | +++ | − | + | − | − | − | − | − | − | − |
| Heart muscle | − | − | − | − | − | − | − | − | − | − | − |
| Kidney | | | | | | | | | | | |
| glomer, basal mem. | − | − | − | − | − | − | − | − | − | +++ | − |
| proximal tubules | +++ | +++ | ++ | + | − | − | − | − | − | − | − |
| thin Henle limbs | + | + | − | − | − | − | − | − | − | − | − |
| large henle limbs | − | − | − | − | − | ++ | ++ | ++ | ++ | ++ | − |

TABLE 2-continued

Immunofluorescent staining of tissues from A– pigs with: Human anti-αGal (αGal); Griffonia simplicifolia 1 isolectin B$_4$ (GSI); anti-B (B); Helix pomatia (HPA); anti-A (A); anti-H (SupH); Ulex europaeus 1 (UEA); anti-H-type-2 (Ht2); anti-H-type-1 (Ht1); peanut agglutinin (PNA) and anti-Le$^x$ (Le$^x$).

| Tissue | αGal | GSI | B | HPA | A | SupH | UEA | Ht2 | Ht1 | PNA | Le$^x$ |
|---|---|---|---|---|---|---|---|---|---|---|---|
| distal tubules | – | – | – | – | – | ++ | ++ | ++ | ++ | ++ | ++* |
| collecting ducts | ± | + | – | – | – | ++ | ++ | ++ | ++ | ++ | – |
| calyces | ± | + | – | – | – | +++ | +++ | +++ | +++ | + | – |
| urinary epithelium | ± | + | – | – | – | +++ | +++ | +++ | +++ | + | – |
| Liver | | | | | | | | | | | |
| duct epithelium | – | – | – | – | – | +++ | ± | + | +++ | + | – |
| hepatocytes | – | + | – | – | – | – | – | – | – | – | – |
| Pancreas | | | | | | | | | | | |
| duct epithelium | + | + | – | – | – | +++ | ++ | ++ | +++ | + | – |
| Langerhans islets | – | – | – | – | – | ++ | – | – | + | ++ | – |
| Lung | | | | | | | | | | | |
| bronchus epithelium | – | – | – | – | – | +++ | +++ | +++ | +++ | + | – |
| seromucous glands | + | + | – | + | – | +++ | +++ | ++ | ++ | ++ | – |
| bronchiole | +++ | +++ | + | ± | – | + | + | + | ± | ± | – |
| alveoli | ++ | ++ | ++ | ± | – | – | – | – | – | – | – |
| Small intestine | | | | | | | | | | | |
| brush border | – | – | – | – | – | +++ | +++ | +++ | +++ | – | – |
| goblet-cells | – | – | – | + | – | +++ | +++ | +++ | +++ | + | – |
| Skin | | | | | | | | | | | |
| stratum granulosum | – | – | – | – | – | ++ | + | + | – | ++ | – |
| stratum spinosum | + | + | – | + | – | ++ | – | – | – | ++ | – |
| hair follicles | – | – | – | ± | – | ++ | – | – | ± | + | – |
| apocrine glands | – | – | – | ± | – | +++ | +++ | ++ | ± | + | – |

*Only the macula densa in front of the glomerular vascular pole was positive.

The antibodies eluted from the immunoadsorbents containing the structure αGal1-3βGal (the linear-B disaccharide and the two linear-B trisaccharides) gave similar immunofluorescence results. They stained strongly the pig vascular endothelium at 200 μg/ml. Their activity faded with dilution of the antibody and disappeared at 20 μg/ml.

The antibodies obtained with the monosaccharide αGal were only weakly positive at 100 μg/ml, and the antibodies eluted with the *Escherichia coli* receptor disaccharide αGal1→4βGal were negative at 100 and 200 μg/ml. The relative intensity of the reaction of the different fractions of anti-αGal antibodies purified on the five immunoadsorbents were: the two linear-B trisaccharides≈linear-B disaccharide>α-galactose>disaccharide receptor of *Escherichia coli*. This last fraction was weakly positive at higher concentrations.

Immunofluorescence of vascular endothelial cells in myocardium stained with the isolectin B4 from *Griffonia simplicifolia* lectin 1 (FITC-GSIB$_4$). only the vascular endothelium is positive (green). Both A+ and A– pigs give the same staining.

The same positive reactions on vascular endothelium were obtained with the affinity purified lectin 1 from *Griffonia simplicifolia* at 100 μg/ml. This lectin preparation is a random mixture of tetramers of two subunits, A and B, in different proportions (A$_4$, A$_3$B, A$_2$B$_2$, AB$_3$ and B$_4$). A$_4$ reacts strongly with αGalNac and weakly with αGal, while B$_4$ is specific for αGal epitopes, as described by Murphy and Goldstein, "Five α-D-Galactopyranosyl-binding isolectins from *Bandeiraea simplicifolia* seeds" *J. Biol. Chem.* 252, 4739–4742 (1977). A$_4$ and B$_4$, the two purified extreme isolectins, reacted also with vascular endothelium, but isolectin B$_4$ was positive at 10 μg/ml, while isolectin A$_4$ required a hundred times higher concentration to give the same result.

The *Helix pomatia* lectin was also positive on vascular endothelium, but weakly and only at a very high concentration (1 mg/ml).

All the other lectins, monoclonal and polyclonal antibodies were negative on pig heart irrespective of the A+ or A-phenotype of the pig.

Myocardium section treated with neuraminidase and stained with peanut agglutinin (FITC-PNA). All connective tissue is positive (green) and myocytes are negative. Both A+ and A– pigs give the same staining.

The positive reactions on vascular endothelium given by human anti-αGal, *Griffonia simplicifolia* 1 and *Helix pomatia* lectins were abolished by pre-digestion of the tissue with α-galactosidase and were not modified by β-galactosidase, α-fucosidase or neuraminidase. After treatment with neuraminidase the connective tissue around myocytes appeared positive with peanut agglutinin (PNA).

Vascular endothelium had the same positive immunofluorescence reactions with human anti-αGal, *Griffonia simplicifolia* 1 isolectin B$_4$ and *Helix pomatia* in all the other organs studied, irrespective of the A+ or A-phenotype of the pig. However, other organs had in addition positive reactions on other cells (Tables 1 and 2).

The lectin MAA (*Maackia amurensis*), specific for NeuAc α 2→3 Gal β1-R, stains well the pig vascular endothelium, showing that both αNeuAc and αGal epitope are present on pig endothelium.

Kidney.

Cortex of the kidney of an A+ pig double stained with anti-A (FITC) and anti-αGal (TRITC-GSI). Proximal tubules and vascular endothelium are positive with anti-αGal (red). Distal and collecting tubules are positive with anti-A (green). Medulla of the kidney of an A+ pig double stained with anti-A (FITC) and anti-αGal (TRITC-GSI).

Collecting ducts and large limbs of Henle's loop are positive with anti-A (green). Vascular endothelium of the intertubular capillaries and the epithelial cells of the thin limbs of the loops of Henle are positive with anti-αGal (red).

In addition to vascular endothelium, human anti-αGal, *Griffonia simplicifolia* 1 and its isolectin $B_4$ stained strongly the brush border and the cytoplasm of epithelial cells of proximal convoluted tubules and weakly the apical portion of thin Henle limbs and collecting ducts, calyces and urinary epithelium.

The three strongest monoclonal anti-B reagents from the workshop (026, 028 and 046) also stained the renal proximal tubules. These antibodies belong to the cluster which cross-reacts with all linear-B structures containing the terminal disaccharide αGal1→3βGal. Three other anti-B of the same cluster (041, 031 and 032), and the remaining 11 anti-B monoclonals which did not recognize the linear-B antigen, did not stain pig kidney. These anti-linear-B reactions, as those of the vascular endothelium, were independent of the A+ or A-phenotype of the pig and were destroyed by pre-treatment with α-galactosidase.

A dual reaction was observed with *Helix pomatia* in the kidney. Weak anti-linear-B reactivity at high lectin concentration (1 mg/ml), similar to the above described positive pattern on proximal tubules with anti-αGal and anti-linear-B, and strong anti-A reaction at low lectin concentration (10 µg/ml), on distal tubules, collecting ducts, calyces and urinary epithelium of A+ pigs were both documented. The anti-A reactions of *Helix pomatia* was only present on A+ pigs (Table 1). A– pigs were negative (Table 2).

Twelve (001, 002, 005, 006, 012, 013, 016, 018, 020, 049, 050, 052) out of the 18 anti-A monoclonal antibodies were positive on the same cells of the distal convoluted tubules in the cortex, large Henle and collecting ducts in the medulla, calyces and urinary epithelium of A+ pigs (Table 1). These positive anti-A monoclonals corresponded to the strongest antibodies of each of the 6 anti-A clusters defined in the Second International Workshop on Monoclonal Antibodies Against Human Blood Red Cells.

Goat SupH, the four anti-H-type-2 monoclonals, anti-H-type-1 and *Ulex europeaus* lectin 1 were positive on the same cells of A– pigs (Table 2). This fluorescence of anti-H reagents on kidneys from A– pigs was also detected, although very weakly, in the corresponding areas of A+ pigs.

Cortex of the kidney of an A+ pig double stained with *Helix pomatia* (FITC-HPA) and *Ulex europaeus* lectin 1 (TRTC-UEA). Most cells of the distal and collecting tubules are stained by the anti-A activity of *Helix pomatia* (green), but some cells on the same tubules are stained by the anti-H activity of *Ulex europaeus* (red). This micrograph illustrates that some H structures are not transformed into A.

Cortex of the kidney treated with neuraminidase and double stained with peanut agglutinin (FITC-PNA) and *Griffonia simplicifolia* lectin 1 (TRITC-GSI). Glomerular basal membrane and the apical poles of epithelial cells of distal and collecting tubules are stained by PNA (green). Proximal convoluted tubules and vascular endothelium are stained with GSI (red). Both A+ and A– pigs give the same staining.

Due to the fact that the A glycosyltransferase uses the H structure as a substrate to make the A epitope, for each A antigen made, one H antigen is used up; complete transformation of H into A resulted in negative reactions with anti-H reagents in some distal convoluted tubules and collecting ducts of A+ pigs. However, in some epithelial cells incomplete transformation of H into A could be detected by dual simultaneous fluorescence of anti-H in red and anti-A in green.

Peanut agglutinin was positive on the glomerular basal membrane and the apical areas of epithelial cells from distal and collecting tubules. This reaction increased with neuraminidase treatment and was independent of the A+ or A-phenotype of the pig.

Cortex of the kidney stained with anti-Le$^x$ (FITC). Only a very short portion of the distal tubule at the level of the macula densa, in front of the vascular pole of glomeruli, is positive (green). Both A+ and A– pigs give the same staining.

The Le$^x$ antigen was only present on some epithelial cells of the distal convoluted tubule at the level of the macula densa, in a very short segment just in front of the vascular pole of the glomerulus. In humans this antigen is present on epithelial cells of proximal tubules in the same areas of the nephron that are positive with the anti-linear-B in pigs.

Liver.

Liver section of an A+ pig double stained with anti-A (FITC) and *Griffonia simplicifolia* lectin 1 (TRITC). Biliary ducts are positive with anti-A (green). Vascular endothelium is strongly positive and hepatocytes are faintly positive with GSI (red).

Liver section of an A– pig double stained with anti-H-type-1 (FITC) and *Griffonia simplicifolia* lectin 1 (TRITC). Biliary ducts are stained by anti-H-type-1 (green). As in the case described above, vascular endothelium is brighter than hepatocytes with GSI (red).

In A+ pigs, all epithelial cells of biliary ducts were stained strongly with anti-A and *Helix pomatia*, and weakly with SupH, anti-H-type-1 and peanut agglutinin (Table 1). Inversely, in A– pigs all anti-A reagents were negative, and all anti-H reagents were positive on biliary epithelium (Table 2). However, anti-H-type-1 was always stronger than anti-H-type-2, suggesting that type 1 structures are predominant in pig biliary ducts. A similar phenomenon is observed in human liver, where type 1 structures (A, B and H-type-1, Le$^a$ and Le$^b$) are also predominant in biliary ducts.

Hepatocytes did not stain with any of the anti-A or anti-H. They were only weakly and irregularly stained with *Griffonia simplicifolia* lectin 1 in addition to its vascular endothelium staining. Human hepatocytes are not stained by any of these reagents, but they express sialyl-Le$^x$.

Pancreas.

Pancreas section of an A+ pig double stained with anti-A (FITC) and *Griffonia simplicifolia* lectin 1 (TRITC). Large and small ducts are stained with anti-A (green). Vascular endothelium is stained with GSI (red). The apical portion of epithelial cells in large ducts and the intraluminal secretion is stained by both reagents (bright yellow).

Pancreatic ducts of A+ pigs were strongly stained with anti-A and *Helix pomatia* and they were not (or weakly) stained with anti-H (Table 1). The same ducts of A– pigs were negative with anti-A strongly stained with anti-H (Table 2). The vascular endothelium and the apical border of ductal cells were positive with human anti-αGal and *Griffonia simplicifolia* lectin 1 in both A+ and A– pigs.

Small secretory ducts were weakly positive with anti-A in A+ pigs and with anti-H in A– pigs.

Pancreas double stained with SupH (FITC) and *Griffonia simplicifolia* lectin 1 (TRITC). Some cells in the Islets of langerhans are stained with anti-H (green). Vascular endothelium is stained with GSI (red). Both A+ and A– pigs give the same staining.

The cytoplasm of some cells of the islets of Langerhans was positive with SupH, anti-H-type-1 and peanut agglutinin irrespective of the A phenotype of the pig.

Lung.

Lung of an A+ pig double stained with anti-A (FITC) and *Griffonia simplicifolia* lectin 1 (TRITC). The ciliated epithelium of large bronchi and seromucous glands are stained with anti-A (green). Part of the mucous secretion in seromucous glands is stained with GSI (red).

The ciliated epithelium of large bronchi were strongly positive with anti-A and *Helix pomatia* in A+ pigs (Table 1) and with anti-H reagents in A− pigs (Table 2). Seromucous glands were positive with anti-A or anti-H in A+ or A− pigs respectively, and were also positive with the anti-αGal reagents in both types of pigs.

Lung of an A+ pig double stained with anti-A (FITC) and *Griffonia simplicifolia* lectin 1 (TRITC). Only a few cells in the bronchiolar epithelium are stained with anti-A (green). The respiratory epithelium and the great majority of the bronchiolar epithelial cells are stained with GSI (red).

Lung of an A− pig double stained with anti-H (FITC) and *Griffonia simplicifolia* lectin 1 (TRITC). Only a few cells in the bronchiolar epithelium are stained with anti-H (green). The majority of the bronchiolar epithelium is stained with GSI (red).

In both A+ or A− pigs the number of A and H positive epithelial cells decreased progressively with reduction of the size of the bronchi; only a few A or H-positive cells were found in terminal bronchiolar epithelium. The bronchial epithelial cells that did not stain with anti-A or anti-H, did stain with human anti-αGal and *Griffonia simplicifolia* lectin 1. The number of αGal-positive cells increased with the decrease in size of bronchi, and all the final bronchiolar branches and the alveolar respiratory epithelium were stained by anti-αGal reagents and were negative with anti-A or anti-H. The human respiratory epithelium has the blood group I antigen at the places where the pig respiratory epithelium expresses the linear-B antigen.

Small intestine.

Goblet cells and the brush border were strongly positive with anti-A and *Helix pomatia* in A+ pigs (Table 1) and with anti-H reagents in A− pigs (Table 2). In A− pigs, *Helix pomatia* was negative on all cells of surface epithelium and positive on some deep goblet cells. PNA was positive on goblet cells and negative on the brush border of both A+ and A− pigs.

Mucosa of small intestine of an A− pig double stained with *Ulex europaeus* lectin 1 (FITC-UEA) and *Griffonia simplicifolia* lectin 1 (TRITC). Goblet cells and brush border are stained with anti-H (green). Vascular endothelium in the stroma of the villi is stained with GSI (red). Both A+ and A− pigs give the same staining with GSI.

As in all the other pig organs, the vascular endothelium in the stroma of the villi was positive with anti-αGal reagents.

Skin.

All layers of the epidermis and hair follicles were positive with SupH and peanut agglutinin.

Skin double stained with the isolectin $B_4$ from *Griffonia simplicifolia* (FITC-GSIB$_4$) and *Ulex europaeus* lectin 1 (TRITC-UEA). Vascular endothelium in the dermis and deep layers of epidermis are stained with GSIB$_4$ (green). Upper layers of epidermis are stained with UEA (red).

Other reagents were only positive on certain areas. The stratum granulosum was positive with *Ulex europaeus*. The deep layers of the epidermis and the vascular endothelium in the dermis were positive with αGal reagents. The intraluminal content and the epithelial cells of apocrine secretory glands in the dermis were strongly positive with anti-H reagents.

All anti-A reagents were negative on the skin and its appendages and all the epidermal positive staining with other reagents were independent of the A+ or A− phenotype of the pig.

These results indicate that the smallest common structure able to react efficiently with the human natural antibodies is the linear-B disaccharide αGal1→3βGal. Such a small structure has the advantage of being relatively easy to synthesize and provides the possibility of performing exploratory tests in a pig-to-baboon organ transplant model, which is believed to closely resemble the pig-to-human transplant situation.

Modifications and variations of the present invention, a method to produce organs for transplantation, will be obvious to those skilled in the art from the foregoing detailed description. Such modifications and variations are intended to come within the scope of the following claims.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1500 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Mus musculus (x) PUBLICATION INFORMATION:
      (A) AUTHORS: Larsen, Robert D. Rajan, Valanila P. Ruff, Melissa M. Kukowska-Latallo, Jolanta Cummings, Richard D.
        Lowe, John B.
    (B) TITLE: Isolation of a cDNA encoding a murine
        UDP-galactose:eta-D-galactosyl-1,4-N-acetyl-D-
        glucosaminide-alpha-1,3-galactosyltransferase: Expression
        cloning by gene transfer.
    (C) JOURNAL: Proc. Natl. Acad. Sci. U.S.A.
    (D) VOLUME: 86
    (E) ISSUE: November
    (F) PAGES: 8227-8231
    (G) DATE: 1989
    (K) RELEVANT RESIDUES IN SEQ ID NO:1: FROM 1 TO 1500

(xi) SEQUENCE DESCRIPTION: SEQ ID NO:1:

```
CCTTCCCTTG TAGACTCTTC TTGGAATGAG AAGTACCGAT TCTGCTGAAG ACCTCGCGCT    60

CTCAGGCTCT GGGAGTTGGA ACCCTGTACC TTCCTTTCCT CTGCTGAGCC CTGCCTCCTT   120

AGGCAGGCCA GAGCTCGACA GAACTCGGTT GCTTTGCTGT TTGCTTTGGA GGGAACACAG   180

CTGACGATGA GGCTGACTTT GAACTCAAGA GATCTGCTTA CCCCAGTCTC CTGGAATTAA   240

AGGCCTGTAC TACATTTGCC TGGACCTAAG ATTTTCATGA TCACTATGCT TCAAGATCTC   300

CATGTCAACA AGATCTCCAT GTCAAGATCC AAGTCAGAAA CAAGTCTTCC ATCCTCAAGA   360

TCTGGATCAC AGGAGAAAAT AATGAATGTC AAGGGAAAAG TAATCCTGTT GATGCTGATT   420

GTCTCAACCG TGGTTGTCGT GTTTTGGGAA TATGTCAACA GAATTCCAGA GGTTGGTGAG   480

AACAGATGGC AGAAGGACTG GTGGTTCCCA AGCTGGTTTA AAAATGGGAC CCACAGTTAT   540

CAAGAAGACA ACGTAGAAGG ACGGAGAGAA AAGGGTAGAA ATGGAGATCG CATTGAAGAG   600

CCTCAGCTAT GGGACTGGTT CAATCCAAAG AACCGCCCGG ATGTTTTGAC AGTGACCCCG   660

TGGAAGGCGC CGATTGTGTG GGAAGGCACT TATGACACAG CTCTGCTGGA AAAGTACTAC   720

GCCACACAGA AACTCACTGT GGGGCTGACA GTGTTTGCTG TGGGAAAGTA CATTGAGCAT   780

TACTTAGAAG ACTTTCTGGA GTCTGCTGAC ATGTACTTCA TGGTTGGCCA TCGGGTCATA   840

TTTTACGTCA TGATAGACGA CACCTCCCGG ATGCCTGTCG TGCACCTGAA CCCTCTACAT   900

TCCTTACAAG TCTTTGAGAT CAGGTCTGAG AAGAGGTGGC AGGATATCAG CATGATGCGC   960

ATGAAGACCA TTGGGGAGCA CATCCTGGCC CACATCCAGC ACGAGGTCGA CTTCCTCTTC  1020

TGCATGGACG TGGATCAAGT CTTTCAAGAC AACTTCGGGG TGGAAACTCT GGGCCAGCTG  1080

GTAGCACAGC TCCAGGCCTG GTGGTACAAG GCCAGTCCCG AGAAGTTCAC CTATGAGAGG  1140

CGGGAACTGT CGGCCGCGTA CATTCCATTC GGAGAGGGGG ATTTTTACTA CCACGCGGCC  1200

ATTTTTGGAG GAACGCCTAC TCACATTCTC AACCTCACCA GGGAGTGCTT TAAGGGGATC  1260

CTCCAGGACA AGAAACATGA CATAGAAGCC CAGTGGCATG ATGAGAGCCA CCTCAACAAA  1320

TACTTCCTTT TCAACAAACC CACTAAAATC CTATCTCCAG AGTATTGCTG GGACTATCAG  1380

ATAGGCCTGC CTTCAGATAT TAAAAGTGTC AAGGTAGCTT GGCAGACAAA AGAGTATAAT  1440

TTGGTTAGAA ATAATGTCTG ACTTCAAATT GTGATGGAAA CTTGACACTA TTTCTAACCA  1500
```

(2) INFORMATION FOR SEQ ID NO:2:

(i) SEQUENCE CHARACTERISTICS:
        (A) LENGTH: 394 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:

(A) ORGANISM: Mus musculus (xi) SEQUENCE DESCRIPTION: SEQ ID NO:2:

```
Met Ile Thr Met Leu Gln Asp Leu His Val Asn Lys Ile Ser Met Ser
1               5                  10                  15

Arg Ser Lys Ser Glu Thr Ser Leu Pro Ser Ser Arg Ser Gly Ser Gln
            20                  25                  30

Glu Lys Ile Met Asn Val Lys Gly Lys Val Ile Leu Leu Met Leu Ile
            35                  40                  45

Val Ser Thr Val Val Val Phe Trp Glu Tyr Val Asn Arg Ile Pro
    50                  55                  60

Glu Val Gly Glu Asn Arg Trp Gln Lys Asp Trp Phe Pro Ser Trp
65                  70                  75                  80

Phe Lys Asn Gly Thr His Ser Tyr Gln Glu Asp Asn Val Glu Gly Arg
                85                  90                  95

Arg Glu Lys Gly Arg Asn Gly Asp Arg Ile Glu Glu Pro Gln Leu Trp
            100                 105                 110

Asp Trp Phe Asn Pro Lys Asn Arg Pro Asp Val Leu Thr Val Thr Pro
            115                 120                 125

Trp Lys Ala Pro Ile Val Trp Glu Gly Thr Tyr Asp Thr Ala Leu Leu
    130                 135                 140

Glu Lys Tyr Tyr Ala Thr Gln Lys Leu Thr Val Gly Leu Thr Val Phe
145                 150                 155                 160

Ala Val Gly Lys Tyr Ile Glu His Tyr Leu Glu Asp Phe Leu Glu Ser
                165                 170                 175

Ala Asp Met Tyr Phe Met Val Gly His Arg Val Ile Phe Tyr Val Met
            180                 185                 190

Ile Asp Asp Thr Ser Arg Met Pro Val Val His Leu Asn Pro Leu His
            195                 200                 205

Ser Leu Gln Val Phe Glu Ile Arg Ser Glu Lys Arg Trp Gln Asp Ile
    210                 215                 220

Ser Met Met Arg Met Lys Thr Ile Gly Glu His Ile Leu Ala His Ile
225                 230                 235                 240

Gln His Glu Val Asp Phe Leu Phe Cys Met Asp Val Asp Gln Val Phe
                245                 250                 255

Gln Asp Asn Phe Gly Val Glu Thr Leu Gly Gln Leu Val Ala Gln Leu
            260                 265                 270

Gln Ala Trp Trp Tyr Lys Ala Ser Pro Glu Lys Phe Thr Tyr Glu Arg
            275                 280                 285

Arg Glu Leu Ser Ala Ala Tyr Ile Pro Phe Gly Glu Gly Asp Phe Tyr
    290                 295                 300

Tyr His Ala Ala Ile Phe Gly Gly Thr Pro Thr His Ile Leu Asn Leu
305                 310                 315                 320

Thr Arg Glu Cys Phe Lys Gly Ile Leu Gln Asp Lys Lys His Asp Ile
                325                 330                 335

Glu Ala Gln Trp His Asp Glu Ser His Leu Asn Lys Tyr Phe Leu Phe
            340                 345                 350

Asn Lys Pro Thr Lys Ile Leu Ser Pro Glu Tyr Cys Trp Asp Tyr Gln
            355                 360                 365

Ile Gly Leu Pro Ser Asp Ile Lys Ser Val Lys Val Ala Trp Gln Thr
    370                 375                 380

Lys Glu Tyr Asn Leu Val Arg Asn Asn Val
385                 390
```

We claim:

1. A method for making a non-human tissue or organ, wherein the tissue or organ is less susceptible to antibody-mediated rejection by human serum, comprising
    genetically engineering the genome of a non-human mammal to stably include a nucleotide sequence encoding a sialyltransferase or a fucosyltransferase in operable linkage with a promoter,
    wherein expression of the nucleotide sequence in at least some of the cells of an organ of the mammal results in a reduction of 1→3 galactosyl epitopes on the surface of at least some of the cells of the organ of the mammal such that the organ exhibits a decrease in antibody-mediated rejection when exposed to human serum as compared to a mammalian organ of the same species which does not comprise cells expressing the nucleotide sequence.

2. The method of claim 1 wherein the mammal is a pig.

3. The method of claim 2 wherein the nucleotide sequence encodes a sialyltransferase.

4. The method of claim 2 wherein the nucleotide sequence encodes an α 1→3 fucosyltransferase.

5. The method of claim 1 wherein the nucleotide sequence encodes a sialyltransferase.

6. The method of claim 1 wherein the nucleotide sequence encodes α 1→3 fucosyltransferase.

7. The method of claim 1 wherein the mammal lacks, or has reduced amounts of, on the surface of its organ cells, carbohydrate structures selected from the group consisting of α Gal(1→3) β Gal(1→4) β GlcNac (linear B type 2), α Gal (1→3) β Gal (1→4) β Glc (linear B type 6), α Gal(1→3) β Gal (B disaccharide), and α Gal (α-D-galactose).

8. The method of claim 1 wherein the mammal lacks, or has reduced amounts of, on its cell surfaces, carbohydrate structures selected from the group consisting of N-acetyl-β-D-glucosaminide (β GlcNac) and other structures containing a terminal β GlcNac, α-L-Rhamnose and Rhamnose-containing structures, Forssman disaccharides, Forssman trisaccharides, and A carbohydrates.

9. The mammal of claim 1 wherein the α 1→3 galactosyl residues are capped with a carbohydrate selected from the group consisting of sialic acid and fucose.

10. A non-human transgenic mammal,
    wherein the genome of the mammal stably includes a nucleotide sequence encoding a sialyltransferase or fucosyltransferase in operable linkage with a promoter,
    wherein expression of the nucleotide sequence in at least some of the cells of an organ of the mammal results in a reduction of 1→3 galactosyl epitopes on the surface of at least some of the cells of the organ of the mammal such that the organ exhibits a decrease in antibody-mediated rejection when the tissue is exposed to human serum as compared to a mammalian organ of the same species which does not comprise cells expressing the nucleotide sequence.

11. The mammal of claim 10 wherein the mammal is a pig.

12. The mammal of claim 11 wherein the nucleotide sequence encodes a sialyltransferase.

13. The mammal of claim 11 wherein the nucleotide sequence encodes an α 1→3 fucosyltransferase.

14. The animal of claim 10 wherein the nucleotide sequence encodes a sialyltransferase.

15. The animal of claim 10 wherein the nucleotide sequence encodes an α 1→3 fucosyltransferase.

16. The mammal of claim 15 wherein the mammal lacks, or has reduced amounts of, on the surface of its cells, carbohydrate structures selected from the group consisting of α Gal(1→3) β Gal(1→4) β GlcNac (linear B type 2), α Gal (1→3) β Gal (1→4) β Glc (linear B type 6), α Gal(1→3) β Gal (B disaccharide), and α Gal (α-D-galactose).

17. The mammal of claim 10 wherein the mammal lacks, or has reduced amounts of, on its cell surfaces, carbohydrate structures selected from the group consisting of N-acetyl-β-D-glucosaminide (β GlcNac) and other structures containing a terminal β GlcNac, α-L-Rhamnose and Rhamnose-containing structures, Forssman disaccharides, Forssman trisaccharides, and A carbohydrates.

18. The mammal of claim 10 wherein the α 1→3 galactosyl residues are capped with a carbohydrate selected from the group consisting of sialic acid and fucose.

* * * * *